United States Patent
Bergmann

Patent Number: 5,919,632
Date of Patent: Jul. 6, 1999

[54] USE OF POLYCLONAL HUMAN ANTI-HTG AUTOANTIBODIES AS A REAGENT FOR THE CLINICAL DIAGNOSIS OF THYROID AUTOIMMUNE DISEASES AND REAGENT ADDITIVE FOR DETECTING ANTI-HTG AUTOANTIBODIES IN PATIENT SERA

[75] Inventor: Andreas Bergmann, Berlin, Germany

[73] Assignee: B.R.A.H.M.S. Diagnostica GmbH, Berlin, Germany

[21] Appl. No.: 08/894,332

[22] PCT Filed: Feb. 7, 1996

[86] PCT No.: PCT/EP96/00514

§ 371 Date: Oct. 17, 1997

§ 102(e) Date: Oct. 17, 1997

[87] PCT Pub. No.: WO96/25668

PCT Pub. Date: Aug. 22, 1996

[30] Foreign Application Priority Data

Feb. 16, 1995 [DE] Germany .................. 195 05 266

[51] Int. Cl.[6] ................. G01N 33/543; G01N 33/564
[52] U.S. Cl. ............ 435/7.1; 435/7.93; 435/975; 436/500; 436/506; 436/518; 436/547
[58] Field of Search ..................... 435/7.1, 7.93, 435/975; 436/500, 506, 518, 547

[56] References Cited

U.S. PATENT DOCUMENTS 4,818,688  4/1989  Adamich et al. .............. 435/7.93
5,501,955  3/1996  Bergman .................. 435/7.93

FOREIGN PATENT DOCUMENTS 2265713  10/1993  United Kingdom .
92 21031  11/1992  WIPO .

OTHER PUBLICATIONS

Copy of PL 162 445 with English translation of Polish patent claims only.

Primary Examiner—David Saunders
Attorney, Agent, or Firm—Pillsbury Madison & Sutro, LLP

[57] ABSTRACT

Use of polyclonal human autoantibodies against thyroglobulin (anti-hTg autoantibodies), in particular in the form of an affinity-purified IgG fraction, as a specific binding reagent in an immunological assay for the clinical detection of autoantibodies against thyroglobulin (anti-hTg autoantibodies) in the serum of a patient, in particular in competitive assays in which the anti-hTg autoantibodies to be determined and present in the sample and the polyclonal human anti-hTg autoantibodies used as the specific binding reagent compete for the binding sites of a human thyroglobulin (hTg) used as a further reagent of the assay, one of the stated reagents in each case being labelled and the other component in each case being bound to a solid phase, and in which the presence of the anti-hTg autoantibodies to be determined and present in the sample is detected on the basis of the reduction of the binding of the labelled reagent to the solid phase.

10 Claims, 4 Drawing Sheets

USE OF POLYCLONAL HUMAN ANTI-HTG AUTOANTIBODIES AS A REAGENT FOR THE CLINICAL DIAGNOSIS OF THYROID AUTOIMMUNE DISEASES AND REAGENT ADDITIVE FOR DETECTING ANTI-HTG AUTOANTIBODIES IN PATIENT SERA

The present invention relates to the detection of antibodies in biological fluids with the aid of immunological assays which are carried out with the aid of reagent kits which are produced on an industrial scale and sold by producers of diganostic agents. In particular, the present invention relates to the detection of autoantibodies, in particular autoantibodies against the autoantigens of the thyroid, in which in turn the determination of human autoantibodies against thyroglobulin (hTg) in a human serum or plasma is of primary importance in connection with the present invention.

Thyroglobulin is one of the thyroid autoantigens and is a high molecular weight protein which consists of two identical glycosylated subunits having a molecular weight of about 330 kD each (cf. for example J. Furmaniak and B. Rees Smith in: Autoimmunity, 1990, Vol. 7, pages 63–80). Thyroglobulin is a principle component of the thyroid colloid and is a precursor of the thyroid hormones triiodothyronine ($T_3$) and thyroxine ($T_4$). As a preliminary stage to the synthesis of the stated thyroid hormones, unbound circulating iodine or iodide is incorporated in tyrosyl radicals or iodotyrosine radicals of the Tg under catalytic action of the enzyme thyroidperoxidase (TPO). The thyroid hormones $T_3$ and $T_4$ are then liberated from the iodinated thyroglobulin, this being effected by hormonal control mechanisms which respond to the content of $T_3$ or $T_4$ in the blood.

In the case of thyroid autoimmune diseases, in particular in the case of the destructive Hashimoto's thyroiditis leading to hypothyroidism, in addition to autoantibodies against thyroidperoxidase considerable amounts of autoantibodies against thyroglobulin are detected in the patients' blood (such antibodies are always referred to below as "anti-hTg autoantibodies"). The detection and the quantitative determination of such anti-hTg autoantibodies are thus of considerable importance in the clinical diagnosis of thyroid diseases.

The determination of anti-hTg autoantibodies in patient sera is possible by various techniques, including immunological assays. In a commercially available assay of this type (HENNINGtest® anti-Tg), prediluted serum samples are incubated in the test tubes simultaneously with a labelled Tg (as tracer) and a protein A suspension. If anti-hTg autoantibodies are present in the sample, they react with the antigen hTg added as the tracer. At the same time, the protein A present in the form of particles of a suspended solid phase unspecifically binds to the Fc subunits of the antibodies, and a sandwich complex is formed. The particles of the solid-phase suspension with all molecules bound thereto are converted into a sediment by centrifuging, and the supernatant containing the unbound tracer is removed. The larger the amount of autoantibodies in the sample, the greater the amount of tracer which is bound. The concentration of the anti-hTg autoantibodies is thus directly proportional to the amount of tracer detectable in the sediment, for example to the radioactivity measurable in the sediment in the case of radiolabelling.

By using the unspecific binding partner protein A, with the aid of which whole classes of IgG antibodies can be bound without distinction, and by the simultaneous use of labelled thyroglobulin as a tracer, all anti-hTg autoantibodies are detected in the assay described. Since it is known that patient sera may also contain anti-hTg autoantibodies which cannot be directly associated with a clinically manifest thyroid autoimmune disease, assays which respond selectively to such anti-hTg autoantibodies which are directly linked with, and are the cause of clinically manifest thyroid diseases, such as, for example, Hashimoto's thyroiditis, would also be of interest per se. Moreover, the fact that the known method described requires a centrifuging step may be regarded as a certain disadvantage of said method. However, another method which works as a competitive assay and, as a coated tube method, manages without a centrifuging step (DYNOtest® anti-TPO; cf. DE 41 20 412 C1 with regard to the principle of the method) is available for the determination of anti-TPO autoantibodies, which is very frequently carried out parallel to the determination of anti-hTg autoantibodies. However, simultaneously carrying out two assays which involve different handling steps proves to be a disadvantage in clinical laboratory practice. It would therefore be desirable per se also to be able to carry out the determination of anti-hTg autoantibodies by an assay which works according to the coated tube technique and is a competitive assay and in which the presence of the antibodies to be determined in the investigated serum sample manifests itself as a reduction of the binding of the labelled reagent (tracer) to the walls of a test tube.

While the epitopes of the antigen hTPO are essentially known in the case of the determination of anti-TPO autoantibodies and it is possible to find a set of monoclonal antibodies which are suitable for a competitive determination (cf. Jean Ruf, Marie-Elisabeth Toubert, Barbara Czarnocka, Josée-Martine Durand-Gorde, Mireille Ferrand and Pierre Carayon, in: Endocrinology, Vol. 125, No. 3, pages 1211–1218, 1989), the development of comparable competitive assays has to date come up against fundamental problems in cases where the antigens are very large and/or insufficiently characterized with regard to their epitopes involved in the immunoreaction or where said epitopes are even unknown. Such cases are very numerous, and glutamate decarboxylase (diabetes type I), the acetylcholine receptor (myasthenia gravis), the so-called "myelin basic protein" (multiple sclerosis), the TSH receptor and in particular thyroglobulin (hTg) may be mentioned as examples of such antigens.

If an attempt is made to develop, for the determination of anti-hTG autoantibodies, a competitive assay which corresponds to the method described above for the determination of anti-TPO autoantibodies, difficulties are encountered in connection with the peculiarities of the thyreoglobulin acting as an antigen or the antibody populations formed against thyroglobulin. As mentioned at the outset, human thyroglobulin (hTg) is a very large protein antigen having a very large number of potential antigen determinants (epitopes) which, with the use of human thyroglobulin for producing heterologous antibodies by direct immunization of an animal, result in a population of polyclonal antibodies being obtained which were found to be directed against a large number of different epitopes of human thyroglobulin. However, investigations in recent years have shown that the anti-hTg autoantibodies formed during autoimmune diseases are evidently formed only against a limited number of epitopes on the thyroglobulin surface (J. Furmaniak and B. Rees Smith, in: Autoimmunity, 1990, Vol. 7, pages 63–80; J. Ruf, Mireille Henry, Catherine De Micco, P. Carayon, in: Thyroglobulin and Thyroglobulin Antibodies in the Follow-up of Thyroid Cancer and Endemic Goiter (Hüfner, M., and Reiners, C., Editors), pages 21–31, 1987, G. T. Verlag Stuttgart, New York; C. T. J. Chan, P. G. H. Byfield, R. L. Himsworth and P. Shepherd, in: Clin.exp.Immunol. (1987) 70, pages 516–523; S. M. McLachlan, U. Feldt-Rasmussen, E. T. Young, S. L. Middleton, M. Blichert-Toft, K. Siersboek-Nielsen, J. Date, D. Carr, F. Clark and B. Rees Smith, in: Clinical Endocrinology (1987), 26, pages 335–346; Q. Dong, M. Ludgate and G. Vassart, in: Journal of Endocrinology (1989) 122, pages 169–176; M. E. Devey, K. M. Bleasdale-Barr, S. M. McLachlan, J. Bradbury, F. Clark and E. T. Young, in: Clin.exp.Immunol. (1989), 77, pages 191–195; N. Fukuma, S. M. McLachlan, V. B. Petersen, P. Kau, J. Bradbury, M. Devey, K. Bleasdale, P. Grabowski and B. Rees Smith, in: Immunology 1989, 67, pages 129–131; N. Fukuma, S. M. McLachlan, V. B. Petersen, K. Beever and B. Rees Smith, in: Autoimmunity, 1990, Vol. 6, pages 37–45; Shannon L. Gleason, Patricia Gearhardt, Noel R. Rose and Rudolf C. Kuppers, in: The Journal of Immunology, Vol. 145, No. 6, pages 1768–1775, 1990; Herbert S. Bresler, C. Lynne Burek and Noel R. Rose, in: Clinical Immunology and Immunopathology, Vol. 54, pages 64–75, (1990); Herbert S. Bresler, C. Lynne Burek, William H. Hoffman and Noel R. Rose, in: Clinical Immunology and Immunopathology, Vol. 54, pages 76–86, (1990); Mireille Henry, Yves Malthièry, Eric Zanelli and Bernadette Charvet, in: The Journal of Immunology, Vol. 145, No. 11, pages 3692–3698, 1990; Shigeki Sakata, Toru Ogawa, Yasuyoshi Kimata, Hiroshi Takuno, Hiroshi Maekawa, Masafumi Matsuda, Osamu Tarutani and Kenji Okuda, in: Molecular and Cellular Endocrinology, 79, (1991), pages 93–98; Gilles Dietrich, Martine Pierchaczyk, Bernard Pau and Michel D. Kazatchkine, in: Eur. J. Immunol. 1991, 21, pages 811–814; Yves Malthièry, Mireille Henry and Eric Zanelli, in: FEBS Letters, Vol. 279, No. 2, pages 190–192 (1991); E. Schulz, G. Benker, H. Bethäuser, L. Stempka and M. Hüfner, in: J. Endocrinol. Invest 15, pages 25–30, 1992; Asmae Alami Harchali, Paul Montagne, Marie L. Cuillière, Majida Bouanani, Bernard Pau and Jean Duheille, in: Clin. Chem. Vol. 38, No. 9, pages 1859–1864 (1992); B. Mallet, P. J. Lejeune, J. Ruf, M. Piechaczyk, C. Marriq and P. Carayon, in: Molecular and Cellular Endocrinology, 88, (1992), pages 89–95; J. M. Hexham, J. Furmaniak, C. Pegg, D. R. Burton and B. Rees Smith, in: Autoimmunity, 1992, Vol. 12, pages 135–141; Rudolf C. Kuppers, Ingrid M. Outschoorn, Robert G. Hamilton, C. Lynne Burek and Noel R. Rose, in: Clinical Immunology and Immunopathology, Vol. 67, No. 1, pages 68–77, 1993; Peter J. Delves, Sandra M. McLachlan, Elizabeth Drewe, Nao Fukuma, Vaughan B. Petersen and Bernard Rees Smith, in: Journal of Autoimmunity (1993), 1, pages 77–91; Patrizio Caturegli, Stefano Mariotti, Rudolf C. Kuppers, C. Lynne Burek, Aldo Pinchera and Noel R. Rose, in: Autoimmunity, 1994, Vol. 18, pages 41–49). Owing to the complexity of the problem, complete epitope mapping has to date been unsuccessful for hTg, the situation being made more difficult by the fact that it has been found that the autoantibodies formed during autoimmune diseases are apparently among the conformative antibodies, which makes the attempt at epitope mapping with the use of monoclonal anti-hTg antibodies of animal origin even more difficult and prevents mapping of the relevant epitopes with the use of recombinant, sequential antibodies (Q. Dong, M. Ludgate and G. Vassart, in: Journal of Endocrinology (1989) 122, pages 169–176). Polyclonal heterologous IgG populations obtained by immunization with the aid of hTg in the sera of animals thus do not correspond to the anti-hTg autoantibody populations occurring in autoimmune diseases and are therefore evidently not very suitable or unsuitable for use in competitive immunological assays.

On the other hand, it has been found that the attempt to use monoclonal anti-hTg antibodies in competitive assays for determining anti-hTg autoantibodies also does not lead to the desired results, namely the development of an assay which determines the proportion of those anti-hTg autoantibodies which are actually associated with the pathological process of an autoimmune disease. The reason for the unsatisfactory results with the use of monoclonal anti-hTg antibodies presumably lies in the fact that the individual epitopes which are involved in the anti-hTg autoantibody formation influence one another to such a small extent on the very large hTg molecule that only fractions of the polyclonal anti-hTg autoantibodies actually present in the patient serum are detected in competitive assays using monoclonal anti-hTg antibodies, and that these fractions do not adequately represent the total pathological process.

Attempts to use monoclonal or recombinant human anti-hTg antibodies instead of monoclonal anti-hTg antibodies of animal origin (cf. GB-A-2 265 713) do not in principle alter this problem.

It has thus been found that the determination of anti-hTg autoantibodies on the basis of existing competitive assays is unreliable and cannot be carried out with sufficient sensitivity.

It is therefore the object of the present invention to design competitive assays of antibodies, in particular competitive assays for the determination of anti-hTg autoantibodies, in such a way that such autoantibodies can be determined with high accuracy and reliability even when these autoantibodies are formed against antigens having a large number of relevant epitopes and are present as a population of polyclonal antibodies.

This object is achieved in the determination of anti-hTg autoantibodies in patient sera according to the invention by the use of polyclonal human autoantibodies against thyroglobulin as a specific binding reagent, in particular affinity-purified polyclonal human IgG autoantibodies against thyroglobulin from sera of human patients who suffer from a thyroid autoimmune disease.

Particularly advantageous methods of the use, according to the invention, of polyclonal anti-hTg autoantibodies are described hereinbelow.

The present invention furthermore relates to a reagent kit for the immunological determination of anti-hTg autoantibodies in patient sera, which is essentially characterized in that it contains affinity-purified anti-hTg autoantibodies (an affinity-purified anti-hTg IgG preparation) in addition to conventional components of such a reagent kit.

In accordance with a very much more general aspect which described hereinbelow, the present invention furthermore relates, still generally, to the use of polyclonal human antibodies for the clinical diagnosis of diseases which are characterized by the occurrence of such antibodies since, as will be explained in more detail, the principles arising out of the determination of anti-hTg autoantibodies are applicable to other applications and it was not possible to establish that polyclonal human antibodies (hIgGs) obtained from the sera of sufferers have already been used as specific binding reagents in commercial reagent kits for carrying out immunological assays.

Where it is stated in the present application that polyclonal human autoantibodies against thyreoglobulin are used as a "specific binding reagent", this means that they are used as reactants in an immunological assay in which a specific immunological reaction between antigen and antibody or antibodies is utilized. "Specific binding reagent" is not used in the meaning of "binder for analytes", since it would be necessary to regard as "analytes" the antibodies to be determined and with which the polyclonal human autoantibodies against thyroglobulin, which are to be used according to the invention, compete as competitors for binding sites of the antigen thyroglobulin.

The present invention is based on the knowledge that it is possible very reliably to detect anti-hTg autoantibodies in the serum of a patient if, instead of using antibodies (polyclonal or monoclonal anti-hTg antibodies) of animal origin, as has been usual to date in the area of the industrial preparation of reagent kits for immunological assays, polyclonal human autoantibodies which are obtained directly from the serum of patients shown to be suffering from the thyroid autoimmune disease to be detected are used. In the present invention, it is possible in general to use such polyclonal human autoantibodies in the form of a serum of an individual patient with the typical symptoms of the thyroid autoimmune disease to be detected, but it is preferable to use the combined ("pooled") sera of a plurality of such patients as a source for the polyclonal human autoantibodies, in order to ensure that the starting serum used contains as complete a population as possible of all autoantibodies which may be formed in humans in connection with the disease to be detected. Furthermore, in the case of the determination of anti-hTg autoantibodies, the polyclonal human autoantibodies are preferably not used in such a way that all IgG autoantibodies present in such a serum are employed; instead, the polyclonal human autoantibodies are preferably used, after affinity purification with the use of a hTg affinity matrix, in such a way that the immunoglobulin fraction used as a specific binding reagent comprises essentially only anti-hTg autoantibodies.

Where the present application refers to the use of thyroglobulin or human thyroglobulin for the purpose of the affinity purification or as a reagent in an immunological assay, what is primarily meant is a conventional human thyroglobulin, as is commercially available from various producers, for example from the British company Scipac. However, since it has recently been shown that very specific thyroglobulin fractions may be involved to an above-average extent in the formation of autoantibodies during thyroid autoimmune diseases (Ali M. Saboori, Noel R. Rose, Rudolf C. Kuppers, Wayne G. Butscher, Herbert S. Bresler and C. Lynne Burek, in: Clinical Immunology and Immunopathology, Vol. 72, No. 1, pages 121–128, 1994; A. Gardas, in: Autoimmunity, 1991, pages 331–336), the present invention expressly uses, both for affinity purification and as a reagent in the assay, not a complete thyroglobulin preparation but only a human thyroglobulin fraction which is particularly important for autoimmune diseases, for example the protein fraction which is designated as protein peak 1 in the stated publication and which corresponds to a thyroglobulin having a greatly reduced degree of iodination, or another fraction of hTg, which can be shown to occur to a greater extent, for example, in those suffering from Hashimoto's thyroiditis than in healthy persons. By using such a thyroglobulin fraction instead of a complete thyroglobulin preparation, it may once again be possible to achieve further advantages with regard to the selectivity and/or sensitivity and specificity of the assay.

The determination, according to the invention, of human anti-hTg autoantibodies is illustrated in more detail below with reference to two Figures and two measured curves and two Use Examples.

In the Figures.

By the use of polyclonal human anti-hTg autoantibodies as specific binding reagents, it is possible to realize competitive immunological assays in which the polyclonal human autoantibodies added as specific binding reagents compete with the autoantibodies to be detected in the patient's sample.

Figure 1:
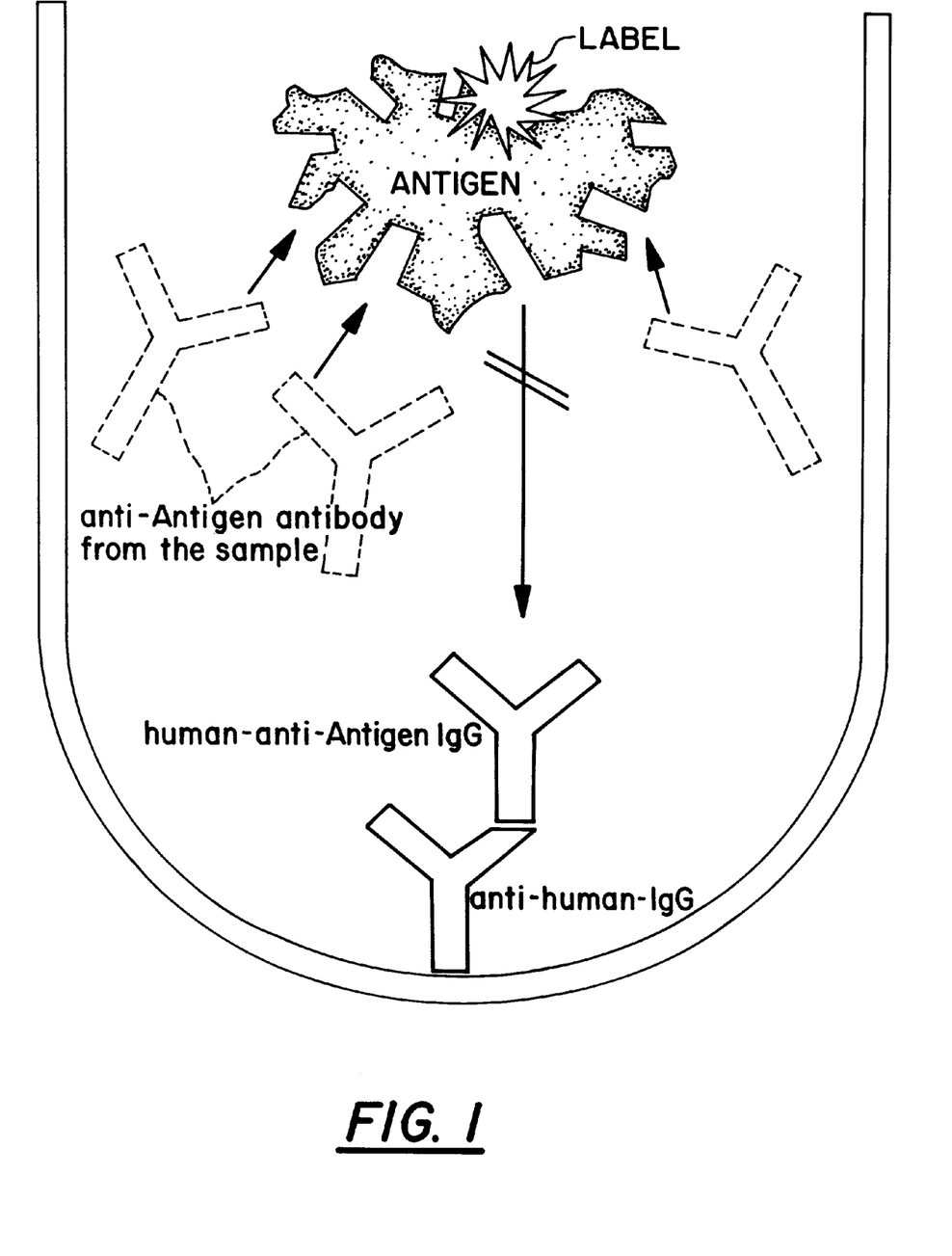
FIG. 1 shows the principle of the method in a first variant of an anti-hTg autoantibody determination using an affinity-purified polyclonal human IgG fraction which serves as an immobilized specific binder for the hTg used in labelled form.

In particular, the assay can be carried out in such a way that (cf. FIG. 1), according to one variant, the polyclonal human anti-hTg autoantibodies, in particular in the form of an affinity-purified anti-hTg-IgG preparation, bind to a solid carrier phase, in particular to the wall of a test tube, and that a labelled human thyroglobulin, for example a radioiodinated human thyroglobulin, is used as a further reagent. In the absence of anti-hTg autoantibodies, in particular in the absence of hTg autoantibodies which are the cause of the thyroid disease to be detected, the labelled thyroglobulin is bound completely or to a percentage characteristic of a blank sample. If anti-hTg autoantibodies of the type to be detected are present in the patient's sample, the result is competition between the antibodies used in the method as a specific binding reagent and the antibodies in the patient's serum, which is manifested in reduced binding of the labelled thyroglobulin to the solid phase, which, after a solid/liquid separation, results in less label being found on the solid phase.

Figure 2:
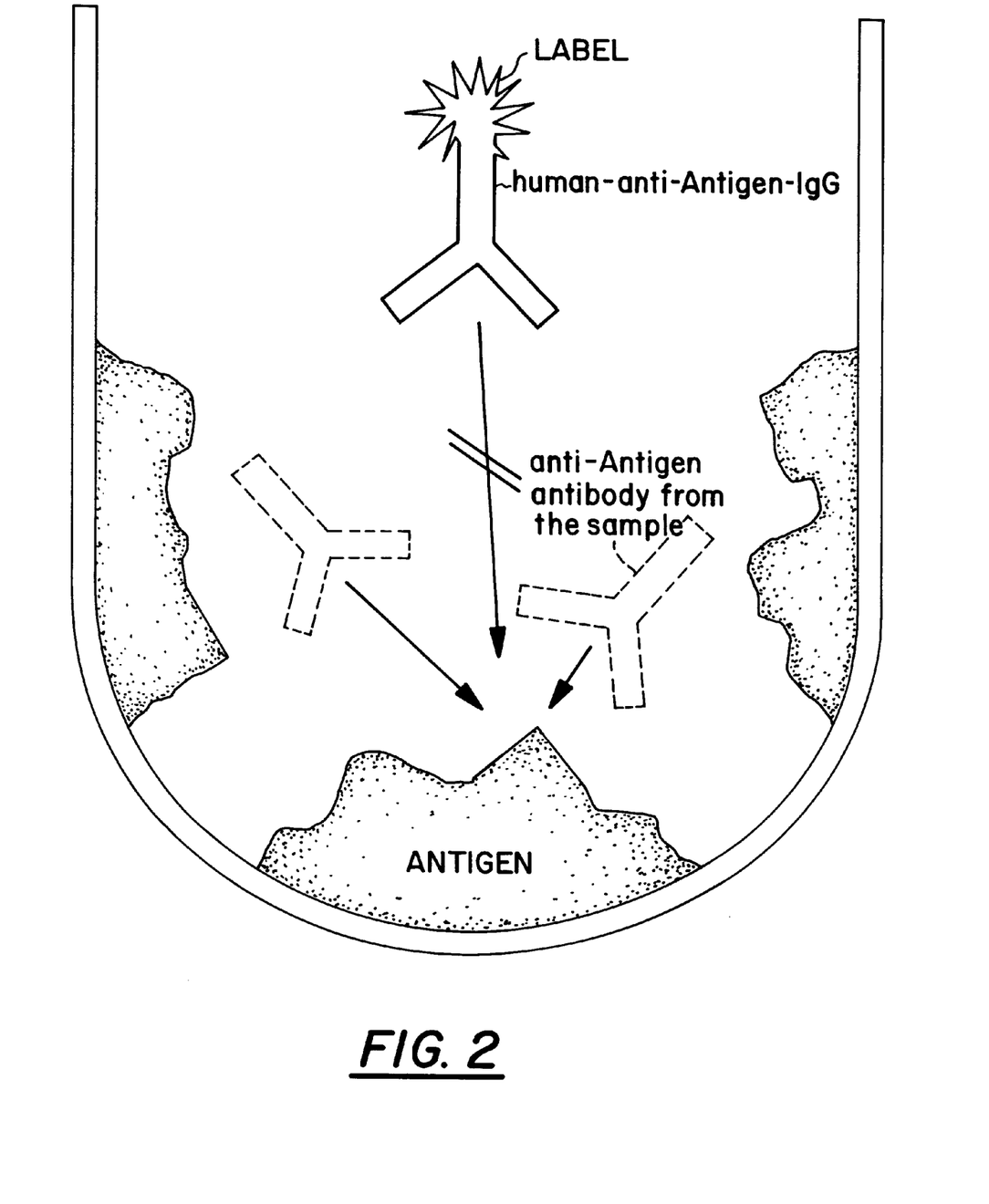
FIG. 2 shows the principle of the method in a second variant of an anti-hTg autoantibody determination using an affinity-purified polyclonal human IgG fraction which is used in labelled form as a specific binder for the hTg used in immobilized form.

In another principle of the method which is also known per se in principle (FIG. 2), it is also possible to follow a procedure in which the antigen, that is to say human thyroglobulin (or a fraction thereof, see above), is immobilized on a solid phase and a tracer in the form of a labelled polyclonal human anti-hTg autoantibody fraction is used. In this case too, the presence of the autoantibodies to be determined in a patient's sample leads to a reduction in the binding of the label to the solid phase.

Even if an iodine radioisotope is always used in the Examples of the present invention as a marker or label for the tracer molecule, it is evident to a person skilled in the art that the nature of the label used is not critical and any other suitable label can be chosen and used for tracer preparation.

The solid phase may also be the wall of a microtitre plate or another coarsely disperse or finely disperse solid phase known per se, and the suitable solid phase can be chosen primarily on the basis of practical considerations for the particular application.

As the tests below show, it has surprisingly been found that a reliable anti-hTg autoantibody determination in human sera is possible by competitive assay with the use of polyclonal human anti-hTg autoantibodies as a specific binding reagent.

The use of polyclonal human anti-hTg autoantibodies as a specific binding reagent presumably has the advantage that binding partners for all possible epitopes which are associated with the pathogenic development of anti-hTg autoantibodies are present on the hTg molecule in such a polyclonal specific binding reagent. However, this ensures that any occurrence of such anti-hTg autoantibodies in a patient's serum leads to a detectable effect, the effect of course increasing with the amount and/or the number of individual autoantibody types in a patient's serum. The possibility, with the use of monoclonal antibodies as a specific binding reagent, that in fact the specific binding between monoclonal antibody and antigen will not be disturbed by a certain type of autoantibody from a patient's serum and such autoantibodies will thus not be detected is not expected in the method according to the invention. By using patients' sera having autoantibodies which are a typical set for a certain disease and, as an antibody population, represent a sort of fingerprint distribution which can be correlated with a certain pathological condition, the optimum possible specificity for such a fingerprint pattern is furthermore obtained, and unspecific side effects can be eliminated by suitable standardization.

When polyclonal human anti-hTg autoantibodies are used, there is sufficient probability that—even with immobilization or labelling of these antibodies or of the associated antigens—all relevant epitopes of hTg are available for binding with all relevant autoantibody types, so that each individual antibody type of the population can make a contribution to the total measured result, the clinical relevance of which is thus increased.

However, a precondition for the present invention was also the surprising discovery that there is in practice no serious problem in working with antibodies obtained from sera of human donors suffering from a disease instead of with antibodies obtained by immunization of animals or with corresponding monoclonal antibodies, as has been usual to date. It was surprisingly found that, for example, anti-hTg autoantibodies are present in sera of patients with Hashimoto's thyroiditis in amounts such that a relatively small amount of donor serum is sufficient to meet the requirement for the preparation of a large amount of coated test tubes. Thus, 5 mg of affinity-purified anti-hTg autoantibodies, which is sufficient for about 25000 individual determinations, can be obtained, for example, using 10 ml of patient's serum with a content of, for example, 10000 U/ml of anti-Tg (determined in the HENNINGtest® anti-Tg of the Applicant). Furthermore, it has surprisingly been found that, when pooled sera of a sufficient, relatively small number of different persons suffering from a disease are used, very suitable polyclonal human autoantibodies with substantially identical binding properties are obtained for the intended use, and relative fluctuations which may be observed from batch to batch can easily be taken into account by means of the envisaged usual calibration steps.

Reservations with regard to adequate availability and/or reproducibility and constancy of quality of the specific binding reagents are therefore unjustified in assays with the use of polyclonal human antibodies. Such reservations— amounting to a prejudice—might explain why human IgG fractions are at present never used in the commercial assays as specific binding partners and why it was also not possible to find in the literature a proposal for the use of polyclonal human IgG fractions as specific binding partners for the preparation of commercial reagent kits for immunological assays for the determination of antibodies in patients' sera.

It is evident from the above statements, in particular with regard to the detection specificity discussed, which is capable of detecting the "fingerprint pattern" of disease-specific antibody populations, that the principle on which the present invention is based is suitable not only for the determination of anti-hTg autoantibodies but generally for antibody determination in clinical diagnosis, and in particular also for the determination of antibodies against external antigens. A possible application of this type consists, for example, in using IgG fractions obtained from an individual patient while suffering from his disease as specific binding partners for assays which are used for monitoring the improvement in the condition of this specific patient on the basis of the reduction in the antibodies circulating in the patient's blood. In such a case, a doctor can be provided with a reagent kit which contains all required reagents except for the test tubes to be coated by the doctor himself with an IgG fraction obtained from the patient. If the doctor prepares a certain stock of such patient-specific test tubes, he is able subsequently to monitor the changes in the antibody concentrations in a patient and possibly the disappearance of the original antibodies.

Similarly, human antibodies against a certain antigen from patients' sera, which have been pooled and if necessary concentrated by affinity purification, can be used to prepare a test system which makes it possible to determine, in a general but clinically highly relevant manner, the immune status of patients who are suspected of suffering from a disease caused by this antigen. Suitable antigens are not only autoantigens but also pathogenic antigens of bacterial or viral origin or antigens which act as allergens. Such test systems may even be provided when very little is known about the antigens and the type of antibodies formed against these antigens, since the test system to a certain extent directly indicates the presence or absence of a corresponding pathogenic condition, provided that this is reflected in a reaction of the immune system with adequate antibody formation.

The present invention is illustrated in more detail below with reference to two examples for the two assay types for anti-hTg autoantibodies shown in the Figures. However, it should also be noted at this point that the principle of the present invention has also proved its worth in other cases where, as in the case of the determination of anti-hTPO autoantibodies, competitive immunological assays with the use of monoclonal antibodies give essentially correct results in the predominant number of cases. With the use of polyclonal human antibodies in the form of an IgG fraction, it was possible to obtain comparable correct results in this case even without prior affinity purification; moreover, in the very rare cases of sera incorrectly determined as antibody-free, the correct result was obtained, indicating that the sera did in fact contain the autoantibodies being searched for.

EXAMPLES

Materials

The tubes used as solid phases in all Examples are tubes from Nunc, Maxisorp quality, 75×12 mm, with star insert.

The buffer solutions mentioned are:

Buffer A: Phosphate-buffered saline solution (PBS), 0.1% Tween 20

Buffer B: 10 mM TRIS HCl, 10 mM NaCl, pH 7.8

Buffer C: 20 mM sodium phosphate, pH 7.0

Buffer D: 25 mM citric acid

Buffer E: 0.5 M sodium phosphate, pH 8.0

Buffer F: 20 mM sodium phosphate, 1% bovine serum albumin (BSA; Sigma), 3% crystallization-inhibited sorbitol syrup (Karion FP; Merck), pH 7.5

Serum samples:

Serum samples from patients with the indications Hashimoto's thyroiditis, autoimmune thyroiditis and Graves'

Disease were obtained from various German hospitals. They were used for the preparation of the reagents or as test sera. Serum samples which are used as control samples are sera from persons who were without symptoms of any infections, autoimmune diseases or allergic diseases.

The assay according to HENNINGtest® anti-Tg, used as a comparative method, is a commercial assay and is available in the form of a reagent kit with working instructions from BRAHMS Diagnostica GmbH, Berlin.

Iodine$^{125}$-labelled human thyreoglobulin was taken from the stated commercial HENNINGtest® anti-Tg.

Affinity purification of anti-hTg autoantibodies from sera of patients with Hashimoto's thyroiditis for preparation of reagents a) Preparation of an affinity matrix 20 mg of human thyroglobulin (Scipac, GB) are dissolved in 7 ml of buffer C, and 100 ml of sodium periodate (Fluka) are added. After incubation for 15 minutes, the solution is desalted by means of NAP 25 columns (Pharmacia) and then mixed with 10 ml of Carbolink material (Pierce, USA). After incubation for 20 hours at 4° C., the material is introduced into a 10 ml glass column (Biorad) and washed with buffer C.

b) Affinity purification of the human anti-Tg autoantibodies from sera of Hashimoto patients 1 ml of serum from each of 10 patients with Hashimoto's thyroiditis are mixed (final anti-hTg content corresponding to a determination with HENNINGtest® anti-Tg of the Applicant: 5000 U/ml) and are circulated for 120 min over the affinity matrix using a peristaltic pump at a flow rate of 1 ml/min. The absorbance of the column outflow is measured continuously at 280 nm. The column is then washed with 50 ml of buffer C.

The human anti-hTg autoantibodies are eluted by washing the column with buffer D. The human anti-hTg autoantibodies (volume after elution: 4 ml) are mixed with 4 ml of buffer E and stored at 4° C. until required for further use.

Example 1

Determination of anti-hTg autoantibodies using a radioiodinated thyreoglobulin as tracer (method HD-R):

a) Preparation of test tubes with human antibodies from patients with Hashimoto's thyroiditis ("HD-R tubes")

Tubes which were coated with anti-human-IgG for binding the human antibodies were first prepared. For this purpose, goat-anti-human-IgG (Order No. 3AG474, Grade 2, from Scantibodies, USA) was diluted in buffer B to a final concentration of 6.7 µg/ml. 300 µl of this solution were pipetted in test tubes (Maxisorp tubes from Nunc) and incubated for 20 h at room temperature. The tube content was then decanted, and the tubes were completely filled with buffer F. After incubation for 2 hours, the tube content was decanted and the tubes were dried in vacuo. The prepared tubes ("AHI tubes") were stored at 4° C.

The human anti-hTg autoantibodies affinity-purified as described above were diluted with buffer A to a protein concentration of 2 µg/ml, and 100 µl of this solution were pipetted into each of the tubes coated with anti-human-IgG (AHI tubes) and incubated for 2 hours with shaking (at 320 revolutions/min) at room temperature. A solution containing 1 mg/ml of human IgG in buffer A is then pipetted to saturate residual free anti-human-IgG binding sites and incubation is continued for a further 2 h with shaking. The tubes are then washed twice with 2 ml of PBS each time and are stored at 4° C. until required for further use.

b) Carrying out the determination

The procedure was based on the following incubation scheme:

1. For the preparation of the samples, dilute human serum of the control groups, and of the patients and of the calibrators in a ratio of 1+20 (one part of serum, 20 parts of buffer) with buffer A.
2. Pipette 100 µl of the sample into the tubes coated with antibodies of patients with Hashimoto's thyroiditis (HD-R tubes).
3. Pipette 100 µl of a radioiodinated human Tg (component of the commercial HENNINGtest® anti-Tg assay).
4. Incubate for 2 hours at room temperature with shaking.
5. Remove the liquid phase and wash twice with 2 ml of PBS each time.
6. Measure the radioactivity remaining in the tubes.

c) Results

Figure 3:
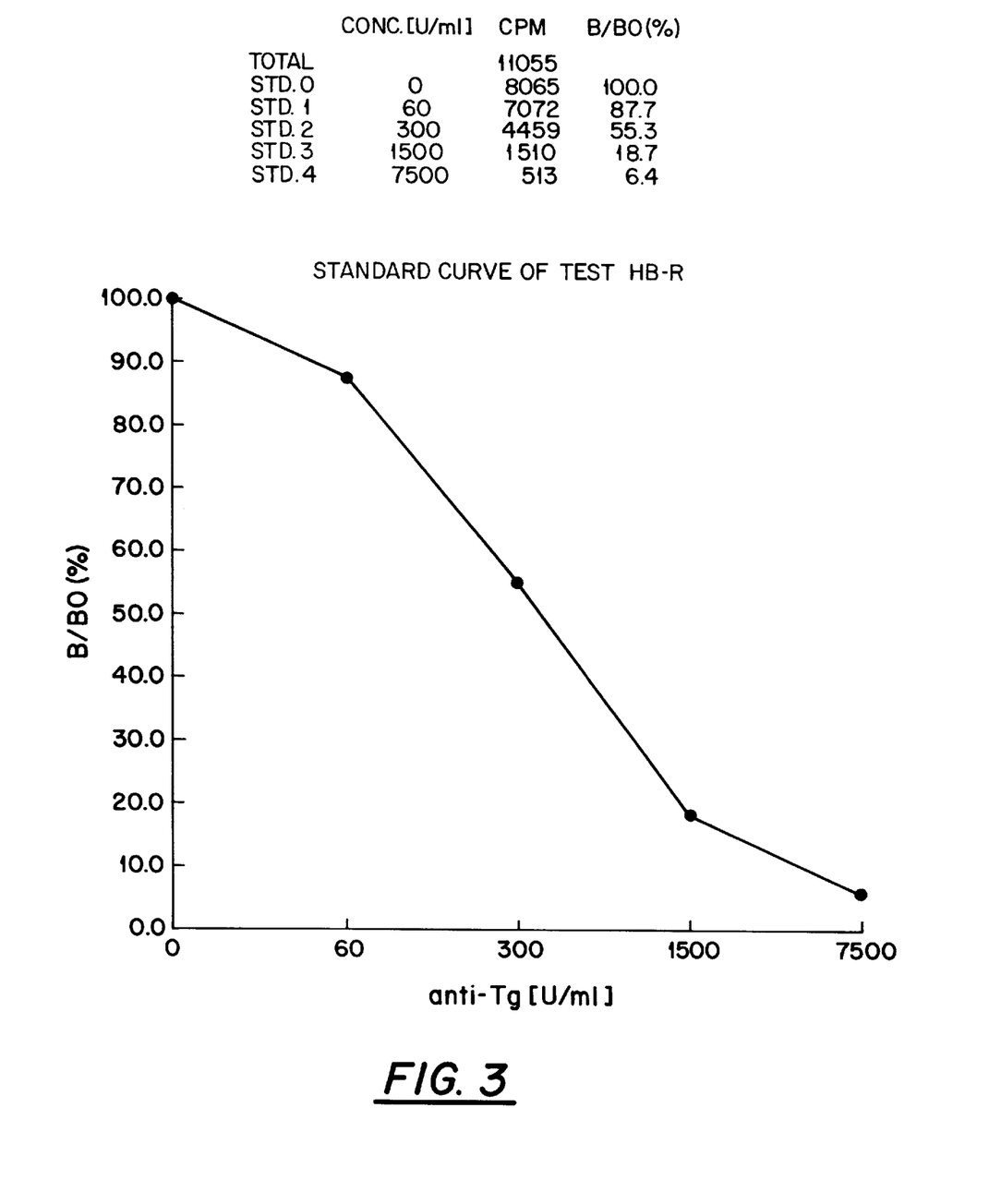
FIG. 3 shows a typical measured curve with associated table of measured values for a determination of anti-hTg autoantibodies in an assay according to Example 1.

In the absence of anti-thyroglobulin autoantibodies in the sample under the stated conditions, the radioiodinated thyroglobulin tracer is bound to an extent of 73% to tubes which are coated with IgG from patients with Hashimoto's thyroiditis. Owing to increasing amounts of anti-Tg autoantibodies in the samples, the binding of the labelled thyroglobulin decreases. Typical measured values of the calibration and a typical measured curve are shown in FIG. 3.

As expected, 41 control samples are found to be negative in the method described, exactly as in the comparative method HENNINGtest® anti-Tg from BRAHMS Diagnostica (cf. Table 1).

85 sera from patients with either Hashimoto's thyroiditis, Graves' Disease or immune thyroiditis were measured in the method according to the invention and in the comparative method HENNINGtest® anti-Tg.

Of the measured samples, which are potentially anti-hTg-positive, 35 samples are found to be positive in the method according to the invention and 32 in the comparative method. 28 samples are found to be positive in both methods. The measured results are listed in Table 2. The results show that the use of polyclonal human anti-hTg autoantibodies is suitable for the determination of autoantibodies against thyreoglobulin in patient sera.

Example 2

Determination of anti-hTg autoantibodies with the use of labelled affinity-purified human anti-hTg autoantibodies from Patient sera (method Tg-R)

a) Radioiodination of human anti-hTg autoantibodies

10 µg of the human anti-hTg autoantibodies affinity-purified as described above and obtained from the sera of patients suffering from Hashimoto's disease, in a volume of 50 µl, are mixed with 50 µl of sodium phosphate buffer, 50 mM, pH 7.4, and 150 µCiNaI$^{125}$I in 2 µl, and the labelling reaction is carried out by the classical Chloramine T method and started by the addition of 2.5 µg of Chloramine T in 5 µl of H$_2$O. After a reaction time of 60 seconds, the sample is diluted with 300 µl of 50 mM sodium phosphate buffer pH 7.4 and desalted by means of an NAP-10 column (Pharmacia) in the usual manner as prescribed. The labelled antibody obtained is diluted with 50 mM sodium phosphate buffer, 0.1% Tween 20, 0.2% BSA, pH 7.4, to a final dilution of 400,000 cpm/ml. The material is stored at 4° C.

b) Procedure

For the determination, the procedure is based on the following incubation protocol:

1. For sample preparation, dilute human serum from control groups, from patients and from calibrators 1+20 with buffer A.
2. Pipette 100 µl of the sample into test tubes coated with thyroglobulin 3. Pipette 100 μl of the radioiodinated human anti-hTg antibody prepared as above
4. Incubate for two hours at room temperature with shaking
5. Separate off the liquid phase and wash the tubes twice with 2 ml of PBS each time
6. Measure the radioactivity remaining in the tubes.

c) Results

Figure 4:
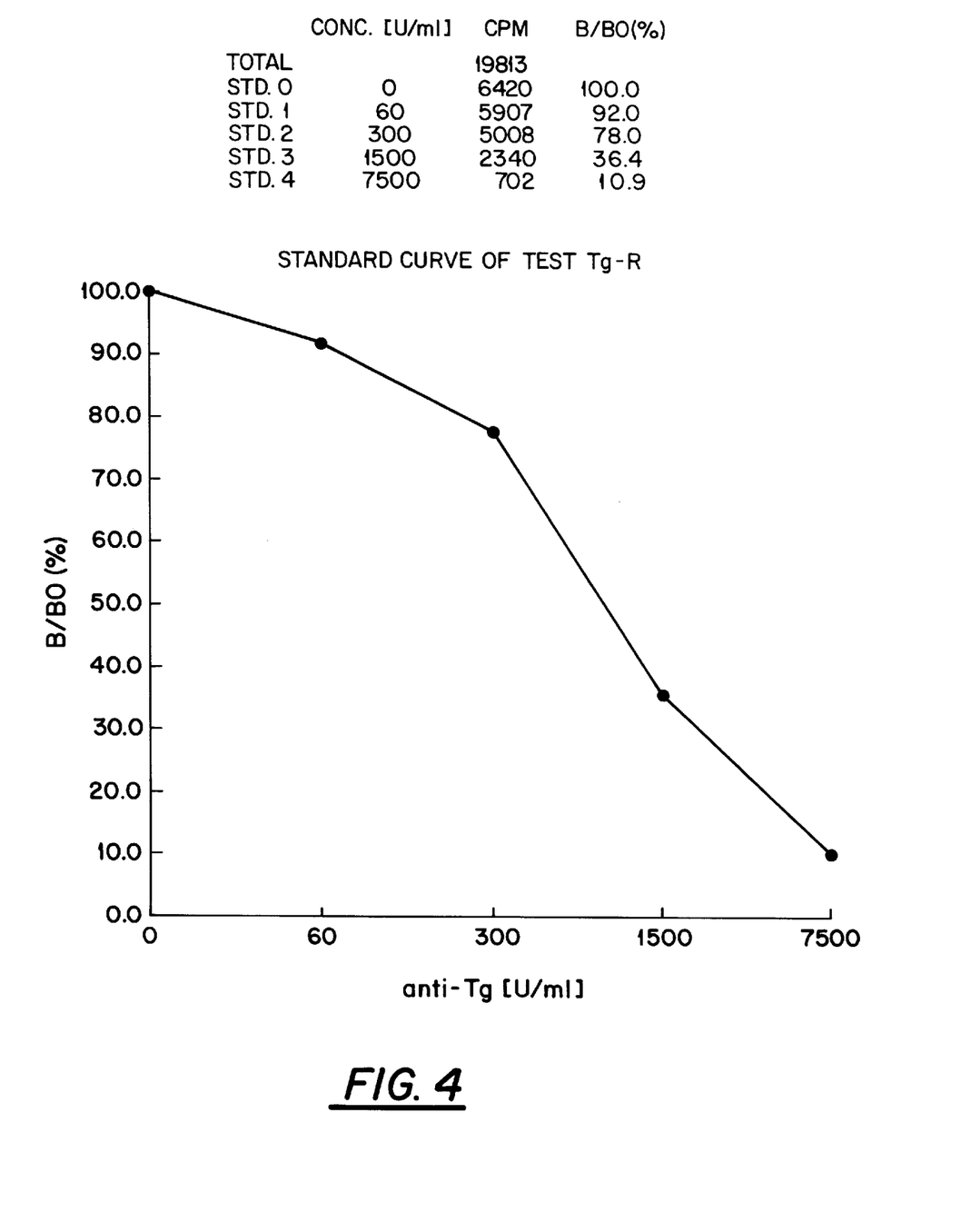
FIG. 4 shows a typical measured curve with associated table of measured values for a determination of anti-hTg autoantibodies in an assay according to Example 2.

In the absence of anti-hTg antibodies in the sample under the stated conditions, the radioiodinated human anti-hTg antibody is bound to an extent of 32% to tubes which are coated with human thyroglobulin (Tg-R). Owing to the increasing amounts of anti-hTg antibodies in the sample, the binding of the labelled human anti-hTg antibody decreases (a typical measured curve is shown in FIG. 4).

As expected, 10 control samples (cf. Table 1) are found to be negative in the method described, as in the comparative method HENNINGtest® anti-Tg from BRAHMS Diagnostica GmbH.

In the measurement of the sera of 85 patients with Hashimoto's thyroiditis, Graves' Disease or immunethyroiditis, 16 samples were determined as being positive by means of the present method. In the comparative method HENNINGtest® anti-Tg, 17 samples were determined as being positive. 14 samples of the present variant of the assay were in agreement with the comparative method HENNINGtest® anti-Tg (cf. Table 2).

It is thus found that it is also possible to use human anti-hTg antibodies obtained from patient sera and present in labelled form for the determination of corresponding autoantibodies against thyroglobulin in patient sera.

TABLE 1

Measurement of control sera

Control group

| No. | Immu anti-Tg U/ml | | HD-R U/ml | | Tg-R U/ml | |
|---|---|---|---|---|---|---|
| 1 | <100 | neg. | <30 | neg. | <60 | neg. |
| 2 | <100 | neg. | <30 | neg. | <60 | neg. |
| 3 | <100 | neg. | <30 | neg. | <60 | neg. |
| 4 | <100 | neg. | <30 | neg. | <60 | neg. |
| 5 | <100 | neg. | <30 | neg. | <60 | neg. |
| 5 | <100 | neg. | <30 | neg. | <60 | neg. |
| 7 | <100 | neg. | <30 | neg. | <60 | neg. |
| 8 | <100 | neg. | <30 | neg. | <60 | neg. |
| 9 | <100 | neg. | <30 | neg. | <60 | neg. |
| 10 | <100 | neg. | <30 | neg. | <60 | neg. |
| 11 | <100 | neg. | <30 | neg. | | |
| 12 | <100 | neg. | <30 | neg. | | |
| 13 | <100 | neg. | <30 | neg. | | |
| 14 | <100 | neg. | <30 | neg. | | |
| 15 | <100 | neg. | <30 | neg. | | |
| 16 | <100 | neg. | <30 | neg. | | |
| 17 | <100 | neg. | <30 | neg. | | |
| 18 | <100 | neg. | <30 | neg. | | |
| 19 | <100 | neg. | <30 | neg. | | |
| 20 | <100 | neg. | <30 | neg. | | |
| 21 | <100 | neg. | <30 | neg. | | |
| 22 | <100 | neg. | <30 | neg. | | |
| 23 | <100 | neg. | <30 | neg. | | |
| 24 | <100 | neg. | <30 | neg. | | |
| 25 | <100 | neg. | <30 | neg. | | |
| 26 | <100 | neg. | <30 | neg. | | |
| 27 | <100 | neg. | <30 | neg. | | |
| 28 | <100 | neg. | <30 | neg. | | |
| 29 | <100 | neg. | <30 | neg. | | |
| 30 | <100 | neg. | <30 | neg. | | |
| 31 | <100 | neg. | <30 | neg. | | |
| 32 | <100 | neg. | <30 | neg. | | |

TABLE 1-continued

Measurement of control sera

Control group

| No. | Immu anti-Tg U/ml | | HD-R U/ml | | Tg-R U/ml | |
|---|---|---|---|---|---|---|
| 33 | <100 | neg. | <30 | neg. | | |
| 34 | <100 | neg. | <30 | neg. | | |
| 35 | <100 | neg. | <30 | neg. | | |
| 36 | <100 | neg. | <30 | neg. | | |
| 37 | <100 | neg. | <30 | neg. | | |
| 38 | <100 | neg. | <30 | neg. | | |
| 39 | <100 | neg. | <30 | neg. | | |
| 40 | <100 | neg. | <30 | neg. | | |
| 41 | <100 | neg. | <30 | neg. | | |

TABLE 2

Measurement of patient sera

Patient sera with following diagnoses: Hashimoto, Graves' disease, immune thyroiditis

| No. | Henningtest anti-Tg U/ml | | HD-R U/ml | | Tg-R U/ml | |
|---|---|---|---|---|---|---|
| 1 | <100 | neg. | <30 | neg. | <80 | neg. |
| 2 | 2156 | pos. | 1350 | pos. | 685 | pos. |
| 3 | 2020 | pos. | 1747 | pos. | 850 | pos. |
| 4 | 1148 | pos. | <30 | neg. | <80 | neg. |
| 5 | 221 | pos. | 422 | pos. | 174 | pos. |
| 6 | 1248 | pos. | 1434 | pos. | 820 | pos. |
| 7 | 4155 | pos. | 4208 | pos. | 4150 | pos. |
| 8 | 1030 | pos. | 870 | pos. | 794 | pos. |
| 9 | 2568 | pos. | 2940 | pos. | 1849 | pos. |
| 10 | 2338 | pos. | 2520 | pos. | 1644 | pos. |
| 11 | <100 | neg. | <30 | neg. | <60 | neg. |
| 12 | 107 | pos. | 158 | pos. | <60 | neg. |
| 13 | 4416 | pos. | 3910 | pos. | 4635 | pos. |
| 14 | 1576 | pos. | 170 | pos. | 144 | pos. |
| 15 | 972 | pos. | 973 | pos. | 620 | pos. |
| 16 | <100 | neg. | <30 | neg. | 333 | pos. |
| 17 | <100 | neg. | 77 | pos. | <60 | neg. |
| 18 | 2467 | pos. | 701 | pos. | 441 | pos. |
| 19 | <100 | neg. | <30 | neg. | <60 | neg. |
| 20 | <100 | neg. | <30 | neg. | <60 | neg. |
| 21 | <100 | neg. | <30 | neg. | <60 | neg. |
| 22 | <100 | neg. | <30 | neg. | 407 | pos. |
| 23 | <100 | neg. | <30 | neg. | <60 | neg. |
| 24 | 963 | pos. | <30 | neg. | <60 | neg. |
| 25 | <100 | neg. | <30 | neg. | <60 | neg. |
| 26 | 170 | pos. | 345 | pos. | 84 | pos. |
| 27 | 724 | pos. | 111 | pos. | 134 | pos. |
| 28 | <100 | neg. | <30 | neg. | | |
| 29 | <100 | neg. | <30 | neg. | | |
| 30 | <100 | neg. | <30 | neg. | | |
| 31 | <100 | neg. | <30 | neg. | | |
| 32 | 2122 | pos. | 223 | pos. | | |
| 33 | 952 | pos. | <30 | neg. | | |
| 34 | 567 | neg. | 94 | pos. | | |
| 35 | 221 | neg. | 318 | pos. | | |
| 36 | <100 | pos. | <30 | neg. | | |
| 37 | <100 | neg. | <30 | neg. | | |
| 38 | 5139 | pos. | 66 | pos. | | |
| 38 | <100 | neg. | 335 | neg. | | |
| 40 | <100 | neg. | <30 | neg. | | |
| 41 | <100 | neg. | <30 | neg. | | |
| 42 | <100 | neg. | 84 | neg. | | |
| 43 | 322 | pos. | <30 | pos. | | |
| 44 | <100 | neg. | <30 | neg. | | |
| 45 | <100 | neg. | <30 | neg. | | |
| 46 | <100 | neg. | <30 | neg. | | |
| 47 | <100 | neg. | <30 | neg. | | |
| 48 | <100 | neg. | <30 | neg. | | |
| 49 | <100 | neg. | 46 | pos. | | |

TABLE 2-continued

Measurement of patient sera

Patient sera with following diagnoses: Hashimoto, Graves' disease, immune thyroiditis

| No. | Henningtest anti-Tg U/ml | | HD-R U/ml | | Tg-R U/ml |
|---|---|---|---|---|---|
| 50 | <100 | neg. | <30 | neg. | |
| 51 | <100 | neg. | 139 | pos. | |
| 52 | 16443 | pos. | 17173 | pos. | |
| 53 | 645 | pos. | 413 | pos. | |
| 54 | <100 | neg. | <30 | neg. | |
| 55 | <100 | neg. | <30 | neg. | |
| 56 | <100 | neg. | <30 | neg. | |
| 57 | <100 | neg. | <30 | neg. | |
| 58 | <100 | neg. | <30 | neg. | |
| 59 | <100 | neg. | <30 | neg. | |
| 60 | <100 | neg. | <30 | neg. | |
| 61 | <100 | neg. | <30 | neg. | |
| 62 | <100 | neg. | <30 | neg. | |
| 63 | <100 | neg. | 69 | pos. | |
| 64 | <100 | neg. | <30 | neg. | |
| 65 | <100 | neg. | <30 | neg. | |
| 66 | 3449 | pos. | 3796 | pos. | |
| 67 | <100 | neg. | <30 | neg. | |
| 68 | 971 | pos. | <30 | neg. | |
| 69 | <100 | neg. | <30 | neg. | |
| 70 | <100 | neg. | 90 | pos. | |
| 71 | <100 | neg. | <30 | neg. | |
| 72 | <100 | neg. | 83 | pos. | |
| 73 | <100 | neg. | <30 | neg. | |
| 74 | 274 | pos. | 207 | pos. | |
| 75 | 156 | pos. | 241 | pos. | |
| 76 | <100 | neg. | <30 | neg. | |
| 77 | 976 | pos. | 42 | pos. | |
| 78 | <100 | neg. | <30 | neg. | |
| 79 | <100 | neg. | <30 | neg. | |
| 80 | <100 | neg. | <30 | neg. | |
| 81 | <100 | neg. | <30 | neg. | |
| 82 | 822 | pos. | 608 | pos. | |
| 83 | 978 | pos. | 285 | pos. | |
| 84 | <100 | neg. | <30 | neg. | |
| 85 | <100 | neg. | <30 | neg. | |

I claim:

1. A method for detection of anti-human thyroglobulin (anti-hTg) autoantibody in a fluid test sample, which method comprises:

(A) combining:
  said test sample,
  a first reagent comprising polyclonal human anti-hTg autoantibodies, and
  a second reagent comprising a human thyroglobulin (hTg) preparation,
    wherein one of said first reagent and said second reagent is a labeled reagent and the other of said first reagent and said second reagent is an immobilized reagent bound to a solid phase;
  under conditions such that
    anti-hTg autoantibody in said test sample, if any, binds to hTg in said hTg preparation, thereby reducing the extent of binding of hTg to said polyclonal human anti-hTg autoantibodies in said first reagent compared to the extent of binding of hTg to said polyclonal human anti-hTg autoantibodies in said first reagent in the absence of said sample, (B) determining the amount of said labeled reagent immobilized on said solid phase by said immobilized reagent, and (C) correlating the amount of said labeled reagent immobilized by said immobilized reagent, if any, in the presence of said test sample with the amount of said labeled reagent immobilized by said immobilized reagent under the same conditions in the absence said test sample, whereby anti-hTg autoantibody in said sample, if any, is detected.

2. A method for determining the amount of anti-human thyroglobulin (anti-hTg) autoantibody in a fluid test sample, which method comprises:

(A) combining:
  said test sample,
  a first reagent comprising polyclonal human anti-hTg autoantibodies, and
  a second reagent comprising a human thyroglobulin (hTg) preparation,
    wherein one of said first reagent and said second reagent is a labeled reagent and the other of said first reagent and said second reagent is an immobilized reagent bound to a solid phase;
  under conditions such that
    anti-hTg autoantibody in said test sample, if any, binds to hTg in said hTg preparation, thereby reducing the extent of binding of hTg to said polyclonal human anti-hTg autoantibodies in said first reagent compared to the extent of binding of hTg to said polyclonal human anti-hTg autoantibodies in said first reagent in the absence of said test sample, (B) determining the amount of said labeled reagent immobilized on said solid phase by said immobilized reagent, and (C) correlating the amount of said labeled reagent immobilized by said immobilized reagent, if any, in the presence of test said sample with the amount of said labeled reagent immobilized by said immobilized reagent under the same conditions in the presence of a fluid reference sample containing a known amount of said hTg, whereby the amount of hTg autoantibody, if any, in said sample is determined.

3. A method according to claim 1 or claim 2, wherein said immobilized reagent comprises said polyclonal human anti-hTg autoantibodies and said labeled reagent comprises human thyroglobulin.

4. A method according to claim 1 or claim 2, wherein said immobilized reagent comprises human thyroglobulin and said labeled reagent comprises polyclonal human anti-hTg autoantibodies.

5. A method according to claim 1 or claim 2, wherein said polyclonal human anti-hTg autoantibodies are provided in the form of a serum obtained from one or more human subjects having a thyroid autoimmune disease wherein serum anti-hTg autoantibodies are produced.

6. A method according to claim 5, wherein said polyclonal human anti-hTg autoantibodies are provided in the form of an anti-hTg-IgG fraction obtained by affinity purification from said serum.

7. A method according to claim 6, wherein said affinity-purified anti-hTg-IgG preparation is obtained from said serum by specific binding to and elution from hTg immobilized on a matrix.

8. A method according to claim 1 or claim 2, wherein said solid phase is the inside wall of a test tube and said human anti-hTg autoantibodies are bound to said inside wall of said test tube by a binder specific for human IgG.

9. A kit for detection of anti-hTg autoantibodies in a fluid sample, which kit comprises a first reagent comprising polyclonal human anti-hTg autoantibodies and a second reagent comprising human thyroglobulin, wherein one of said first reagent and said second reagent is a labeled reagent and the other of said first reagent and said second reagent is an immobilized reagent bound to a solid phase.

10. A kit according to claim 9, wherein said first reagent comprises said polyclonal human anti-hTg autoantibodies comprise an anti-hTg-IgG fraction obtained by affinity purification obtained from serum of one or more human subjects having a thyroid autoimmune disease wherein serum anti-hTg autoantibodies are produced, and said solid phase is the inside wall of a test tube.

* * * * *